(12) United States Patent
Petito

(10) Patent No.: US 10,471,106 B2
(45) Date of Patent: Nov. 12, 2019

(54) COMPOSITION HAVING HYDROLYZED COLLAGEN AND MANUKA HONEY

(71) Applicant: George D. Petito, Bethlehem, PA (US)

(72) Inventor: George D. Petito, Bethlehem, PA (US)

( * ) Notice: Subject to any disclaimer, the term of this patent is extended or adjusted under 35 U.S.C. 154(b) by 0 days.

(21) Appl. No.: 16/059,999

(22) Filed: Aug. 9, 2018

(65) Prior Publication Data

US 2018/0344779 A1   Dec. 6, 2018

Related U.S. Application Data

(63) Continuation-in-part of application No. 15/179,913, filed on Jun. 10, 2016, now abandoned.

(60) Provisional application No. 62/180,583, filed on Jun. 16, 2015.

(51) Int. Cl.
| | |
|---|---|
| *A61K 35/644* | (2015.01) |
| *A61K 47/42* | (2017.01) |
| *A61K 9/06* | (2006.01) |
| *A61K 9/00* | (2006.01) |
| *A61P 17/02* | (2006.01) |
| *A61K 31/11* | (2006.01) |
| *A61K 36/61* | (2006.01) |
| *A61K 38/39* | (2006.01) |

(52) U.S. Cl.
CPC .......... *A61K 35/644* (2013.01); *A61K 9/0014* (2013.01); *A61K 9/0019* (2013.01); *A61K 9/06* (2013.01); *A61K 31/11* (2013.01); *A61K 36/61* (2013.01); *A61K 38/39* (2013.01); *A61K 47/42* (2013.01); *A61P 17/02* (2018.01); *A61K 9/0053* (2013.01)

(58) Field of Classification Search
None
See application file for complete search history.

(56) References Cited

U.S. PATENT DOCUMENTS

| | | | |
|---|---|---|---|
| 7,666,396 B2 | 2/2010 | Lange et al. | |
| 8,303,551 B2 | 11/2012 | Bray et al. | |
| 8,710,289 B2 | 4/2014 | Russell et al. | |
| 2005/0147679 A1* | 7/2005 | Petito | A61K 38/39 424/484 |

FOREIGN PATENT DOCUMENTS

| | | |
|---|---|---|
| CN | 103876996 A | 6/2011 |
| CN | 102319867 A | 2/2012 |
| CN | 102670477 A | 9/2012 |
| CN | 103690396 A | 4/2014 |
| CN | 103816101 A | 5/2014 |
| MX | 2012004016 A | 10/2013 |

OTHER PUBLICATIONS

Mavric et al. (2008) Mol. Nutr Food Res. 52: 483-489. (Year: 2008).*
Visavadia et al. (2008) Brit. J. Oral Maxillofacial Surg. 46: 388-394. (Year: 2008).*
Nzeako et al., "*The Antibacterial Activity of Honey on Helicobacter Pylori*," Seltan Qaboos Univ Med J., Dec. 2006; 6(2):71-76.
Patel et al., "*Manuka honey: an emerging natural food with medicinal use*," www.researchgate.net/publication/246517029_Manuka_honey_an_emerging_natural_food_with_medicinal_use (Last Accessed on May 19, 2016) (pp. 8).
"Satin Smooth Milk 'n Honey Collagen Masks Neck Lift," http://www.amazon.com/Satin-Smooth-HONEY-Collagen-Masks/dp/B00545UORA (Last Accessed on Oct. 22, 2014) (pp. 4).
Any identified foreign patents and/or publications have been properly submitted in parent U.S. Appl. No. 15/179,913, filed Jun. 10, 2016, the priority of which is claimed.

* cited by examiner

*Primary Examiner* — Russell G Fiebig
(74) *Attorney, Agent, or Firm* — Richard C. Litman; Nath, Goldberg & Meyer

(57) ABSTRACT

The composition having hydrolyzed collagen and Manuka honey includes hydrolyzed collagen in an amount ranging from between 5% to 95% by weight and Manuka honey in an amount ranging from between 5% to not greater than 50% by weight in water. The Manuka honey can have a methylglyoxal concentration greater than 100 mg/kg, and preferably greater than 550 mg/kg.

5 Claims, No Drawings

COMPOSITION HAVING HYDROLYZED COLLAGEN AND MANUKA HONEY

CROSS-REFERENCE TO RELATED APPLICATIONS

This application is a continuation-in-part of Ser. No. 15/179,913, filed Jun. 10, 2016, now pending, which application claims the benefit of U.S. Provisional Patent Application Ser. No. 62/180,583, filed Jun. 16, 2015.

BACKGROUND OF THE INVENTION

1. Field of the Invention

The present invention relates to medical compositions, and particularly, to a composition having hydrolyzed collagen and Manuka honey.

2. Description of the Related Art

Honey, made from the nectar of the Manuka tree (tea tree), has exceptional phytochemical-derived, antimicrobial properties, e.g., antibacterial, antifungal, and/or anti-viral properties. In 2008, it was discovered that Manuka honey contains methylglyoxal, and that methylglyoxal gives rise to the antimicrobial properties of Manuka honey. Methylglyoxal has more advantageous properties than the hydrogen peroxide produced in all raw honey from glucose oxidase, which comes from bees during honey production. For example, dietary methylglyoxal is resistant to heat, light, and enzymatic activity, while glucose oxidase/hydrogen peroxide activity is destroyed by heat. Other food items known to contain significant amounts of dietary methylglyoxal are coffee and cocoa (approx. 100 mg/kg). The concentrations of methylglyoxal in coffee and cocoa, however, are small compared to the levels in some Manuka honeys.

Methylglyoxal is found in all honeys in very small concentrations. Manuka honey methylglyoxal contents can range from 0-1000 mg/kg. Anything higher than 100 mg/kg is considered antibacterial, with higher concentrations of methylglyoxal being associated with greater antibacterial activity. A methylglyoxal concentration greater than 400 mg/kg has been proven to kill a large number of powerful bacteria and viruses immune to other classic antibiotics, such as: *Helicobacter pylori*—the bacterium known to cause many stomach and duodenal ulcers; *Staphylococcus aureus* or MRSA—a super-bug with high levels of antibiotic resistance; *Escherichia coli*—known to cause serious food poisoning; and *Streptococcus pyogenes*—causes sore throats. Although it is clear that the dietary methylglyoxal present in many Manuka honeys has strong anti-bacterial properties, its efficacy and safety when ingested is often hotly debated.

Thus, a composition having hydrolyzed collagen and Manuka honey solving the aforementioned problems is desired.

SUMMARY OF THE INVENTION

The composition having hydrolyzed collagen and Manuka honey includes hydrolyzed collagen in an amount ranging from between 5% to 95% by weight and Manuka honey in an amount ranging from between 5% to not greater than 50% by weight in water. The Manuka honey can have a methylglyoxal concentration greater than 100 mg/kg, and preferably greater than 550 mg/kg.

These and other features of the present invention will become readily apparent upon further review of the following specification.

DETAILED DESCRIPTION OF THE PREFERRED EMBODIMENTS

A composition having hydrolyzed collagen and Manuka honey includes about 5% to about 95% hydrolyzed collagen by weight and about 5% to not greater than 50% Manuka honey by weight in water. The composition can be used topically, parenterally, or delivered as either an orally ingestible liquid, tablet or capsule for wound healing, and particularly for the healing of surgical wounds. Throughout the specification the terms Manuka honey and honey have been used interchangeably.

The hydrolyzed collagen can be any suitable type of hydrolyzed collagen having a molecular weight ("MW") ranging from 500 MW to 10,000 MW. Lower MW hydrolyzed collagen can have more cross-linking action with honey than higher MW hydrolyzed collagen. As such, commercially available hydrolyzed collagen having the lowest MW is preferred. The hydrolyzed collagen can be derived from any fish, porcine, bovine, fermentation, or vegetable source. Preferably, the hydrolyzed collagen is derived from a bovine source.

The Manuka honey can be any suitable type of Manuka honey, such as preserved Manuka honey. The Manuka honey can have a methylglyoxal concentration greater than 100 mg/kg, and preferably greater than 550 mg/kg.

The composition can take the physical form used in topical administration, e.g., gel, spray, powder, paste, foam, film, and incorporation in a dressing bandage, a topically applied patch, or in internal administration, e.g., an injectable liquid or orally ingestible liquid.

The composition can be administered to a patient to facilitate wound healing. The Manuka honey in the composition can facilitate control of the bacterial load of a wound and allow the wound bed to have properties similar to those in the extracellular matrix. For example, the methylglyoxal in the Manuka honey can provide antimicrobial properties. The glucose present in the honey is converted to sodium hyaluronate (HA) in a wound environment. HA is a viscoelastic substance consisting of disaccharide chains from glucuronic acid and N-acetylglucosamine. As described below, HA interacts with the hydrolyzed collagen in the extracellular matrix to create an environment conducive to wound healing and, more specifically, to scar-free healing (similar to fetal healing).

The amino groups of the hydrolyzed collagen crosslink with the methylglyoxal in the honey. This cross-linking can allow the hydrolyzed collagen to be time released. For example, availability to the cell site can be demonstrably longer and more controlled than would be if the hydrolyzed collagen is used alone. This cross-linking can also allow immobilization of enzymes and cross-linking with polysaccharides of the HA to produce high density gels and films. In particular, incorporation of saccharides into newly formed collagen is achieved by the cross-linking action of the mono and disaccharides of HA with the hydrolyzed collagen. In effect, the chemotactic attribute of the collagen permits the honey to "transport" more effectively. This happens because collagen is chemotactic: that is, by definition, the characteristic of movement or orientation of an organism or cell along a chemical gradient either toward or away from the chemical stimulus.

Thus, the combination of collagen and honey increases cellular activity due to increased growth factor and cytokine activity through acid activation (acidic pH produced through growth factors such as TGF-B). It is further believed that hydrolyzed collagen offers many advantages to the composition. For example, hydrolyzed collagen has many more active chemical sites than native collagen and affords more control by virtue of its molecular weight. The use of hydrolyzed collagen can be imperative for achieving the cross-linking described above, which limits the reticular (net-like) pattern to the extent necessary for both wound healing and scar reduction. In contrast, collagen (Type 1) occurs only in "parallel," and not mesh-like, filaments, and cross-linking is severely inhibited. The hydrolyzed collagen, as stated previously, is chemotactic thereby allowing for additional chemical activity and possessing the ability to "transport" the reacted honey. While the amount of the hydrolyzed collagen can vary from about 5% to about 95% by weight, the amount of Manuka honey cannot exceed 50% by weight. The use of Manuka honey greater than 50% would deter the wound healing process by overwhelming the synergistic effect it has with the hydrolyzed collagen. The use of the two components in the discussed amounts allows for greater occlusion, flexibility, moisture retention, and water resistance, than either one alone.

The composition can be prepared in any suitable manner, and is not limited to the method described herein. Hydrolyzed collagen is transformed from the powder state to a highly viscous gel, similar to the "as conceived" honey. The initial stages involve heating injection grade water to approximately 135-145° F., and adding the collagen powder while stirring at approximately 35-45 rpm. Once the desired viscosity is achieved (visual and with activity level by formulary), the honey is added at 130° F. or less, but not less than 115° F. It is considered most preferable that the temperature of the honey is between 120-125° F. The antimicrobial benefits of the honey are temperature sensitive and decrease considerably at higher temperatures. It must be noted that viscosity is dependent on the molecular weight of the hydrolyzed collagen and the amount of honey added. It is imperative that the temperature be kept constant to achieve a final product that meets both viscosity and antimicrobial specification(s). The amount of hydrolyzed collagen can vary from between 5% to 95% by weight and the amount of Manuka honey can vary from between 5% to not greater than 50% by weight. The water injected into the composition can include varying degrees of crosslinking and antibacterial effectiveness. The final product(s) can be aseptically filled or post sterilized, but not required.

The presence of Manuka honey in the composition confers a number of additional benefits. The Manuka honey acts like a plasticizer, impacting the drying rate and conforming rate of the resulting collagen gel. Manuka honey also assists in blood clotting. The antibacterial/antimicrobial benefits of the Manuka honey are not discretionary. That is, these attributes "kill" good as well as bad cells, thereby deterring the wound healing process. The disclosed combination of the Manuka honey and hydrolyzed collagen in the amounts specified synergistically supports faster wound healing.

It is to be understood that the present invention is not limited to the embodiments described above, but encompasses any and all embodiments within the scope of the following claims.

I claim:

1. A method of making a homogenized gel composition comprising hydrolyzed collagen and Manuka honey, the method comprising the steps of:
    (a) heating water to a temperature ranging from between 135° F. to 145° F.;
    (b) mixing the heated water with hydrolyzed collagen powder to form a viscous gel;
    (c) maintaining the viscous gel at a constant temperature;
    (d) heating the Manuka honey to between 115° F. and 130° F.; and
    (e) adding the Manuka honey to the viscous gel to form said homogenized gel composition,
    wherein the hydrolyzed collagen ranges from between 5% to 95% by weight of the composition and the Manuka honey ranges from between 5% to 50% by weight of the composition.

2. The method of making a composition having hydrolyzed collagen and Manuka honey according to claim 1, wherein the Manuka honey is heated to between 120° F. to 125° F.

3. The method of making a composition having hydrolyzed collagen and Manuka honey according to claim 1, wherein said Manuka honey has a concentration of methylglyoxal of at least 100 mg/kg.

4. The method of making a composition having hydrolyzed collagen and Manuka honey according to claim 1, wherein said Manuka honey has a concentration of methylglyoxal of at least 550 mg/kg.

5. The method of making a composition having hydrolyzed collagen and Manuka honey according to claim 1, wherein said hydrolyzed collagen has a molecular weight between 500 and 10,000 Daltons.

* * * * *